US008821920B2

(12) United States Patent
Müller

(10) Patent No.: US 8,821,920 B2
(45) Date of Patent: Sep. 2, 2014

(54) THERAPEUTIC PATCH FOR TRANSDERMAL DELIVERY OF CAPSAICIN

(75) Inventor: Walter Müller, Andernach (DE)

(73) Assignee: LTS Lohmann Therapie Systeme AG, Andernach (DE)

( * ) Notice: Subject to any disclaimer, the term of this patent is extended or adjusted under 35 U.S.C. 154(b) by 2174 days.

(21) Appl. No.: 10/823,119

(22) Filed: Apr. 12, 2004

(65) Prior Publication Data
US 2004/0202707 A1 Oct. 14, 2004

Related U.S. Application Data

(60) Provisional application No. 60/462,630, filed on Apr. 14, 2013.

(51) Int. Cl.
A61F 13/02 (2006.01)
A61L 15/16 (2006.01)
A61F 13/00 (2006.01)
A61K 9/70 (2006.01)
A61L 15/00 (2006.01)

(52) U.S. Cl.
USPC ........... 424/448; 424/449; 424/443; 424/445; 424/446; 424/447

(58) Field of Classification Search
None
See application file for complete search history.

(56) References Cited

U.S. PATENT DOCUMENTS

| 3,946,106 | A | | 3/1976 | Chien et al. |
| 4,053,580 | A | | 10/1977 | Chien et al. |
| 4,814,184 | A | | 3/1989 | Aguadisch et al. |
| 5,071,657 | A | * | 12/1991 | Oloff et al. ............. 424/486 |
| 5,145,682 | A | | 9/1992 | Chien et al. |
| 5,494,680 | A | * | 2/1996 | Peterson ................. 424/448 |
| 5,762,963 | A | | 6/1998 | Byas-Smith |
| 5,788,983 | A | * | 8/1998 | Chien et al. ............. 424/449 |
| 6,239,180 | B1 | * | 5/2001 | Robbins ................. 514/627 |
| 6,248,788 | B1 | | 6/2001 | Robbins et al. |
| 6,348,501 | B1 | * | 2/2002 | Holt et al. ............... 514/627 |
| 6,818,671 | B1 | * | 11/2004 | Embil et al. ............. 514/605 |
| 7,063,860 | B2 | * | 6/2006 | Chancellor et al. ..... 424/450 |
| 7,247,315 | B2 | * | 7/2007 | Brown et al. ............ 424/448 |
| 2004/0175344 | A1 | | 9/2004 | Woller |
| 2004/0202710 | A1 | * | 10/2004 | Muller .................... 424/449 |
| 2005/0079206 | A1 | * | 4/2005 | Schacht et al. .......... 424/449 |

FOREIGN PATENT DOCUMENTS

| DE | 10114382 A1 | | 3/2001 |
| WO | WO 01/01967 A1 | | 1/2001 |
| WO | WO 0101967 A1 | * | 1/2001 |

OTHER PUBLICATIONS

Robbins (Treatment of intractable pain with topical large-dose capsaicin: Preliminary report), Anesth Analg 1998; 86: 579-83.*
"Capsaicin Pepper", Prometheus Springs, web downlard 2013.*

* cited by examiner

Primary Examiner — Isis Ghali
(74) Attorney, Agent, or Firm — Frommer Lawrence & Haug LLP

(57) ABSTRACT

The invention relates to a topical patch comprising a therapeutic compound-impermeable backing layer, a self-adhesive matrix based on polysiloxanes and containing capsaicin or a therapeutic compound analogous to capsaicin, and a protective film to be removed before use, in which the matrix contains liquid microreservoirs based on an amphiphilic solvent, in which the therapeutic compound is present in completely dissolved form and the concentration of the therapeutic compound in the microreservoir droplets is below the saturation concentration. The invention furthermore relates to a process for its production and its use in the treatment of neuropathic pain.

15 Claims, 1 Drawing Sheet

- backing layer
- reservoir containing active compound solution
- backing layer
- skin adhesive layer
- removable protective layer

- backing layer
- self-adhesive, active compound-containing matrix
- removable protective layer

- backing layer
- active compound-containing layer with microreservoirs
- removable protective layer

THERAPEUTIC PATCH FOR TRANSDERMAL DELIVERY OF CAPSAICIN

This application claims priority from provisional application 60/462,630, filed Apr. 14, 2013.

BACKGROUND

Neuropathic pain is believed to result from sensitization reactions in the peripheral and central nervous system. Such pain can occur as a result of peripheral injuries, or as a result of systemic diseases such as HIV, herpes zoster, syphilis, diabetes and autoimmune diseases. Neuropathic pain can be severe and is often debilitating, and effective methods for reducing neuropathic pain would ameliorate significant suffering.

In U.S. Pat. No. 6,248,788 (Robbins et al.), a topical method of treatment of neuropathic pain with capsaicin or substances analogous to capsaicin is described. The Robbins et al. patent disclosed that treatment of the affected body areas once or at most twice with a highly concentrated capsaicin preparation for a few hours eliminates or significantly alleviates the pain for a number of weeks. It is believed the basis for this treatment is that the nerve fibers necessary or responsible for the pain sensation (C fibers) are desensitized by the capsaicin (or capsaicin analog) and degenerate. However, this effect only occurs when the active compound concentration in the C fibers is high enough. Conventional topical preparations containing capsaicin do not optimally fulfill these requirements, as they release too little capsaicin on the skin and the active compound concentration in the C fibers remains below the effective concentration.

U.S. Pat. No. 6,239,180 (Robbins) describes the use of therapeutic patches comprising capsaicin and/or a capsaicin analog at a concentration of greater than 5% to 10% by weight for treatment of neuropathic pain. The object was thus to develop a patch which is suitable and optimized for the topical therapy of neuropathic pain and other conditions.

DETAILED DESCRIPTION

Figure 1:
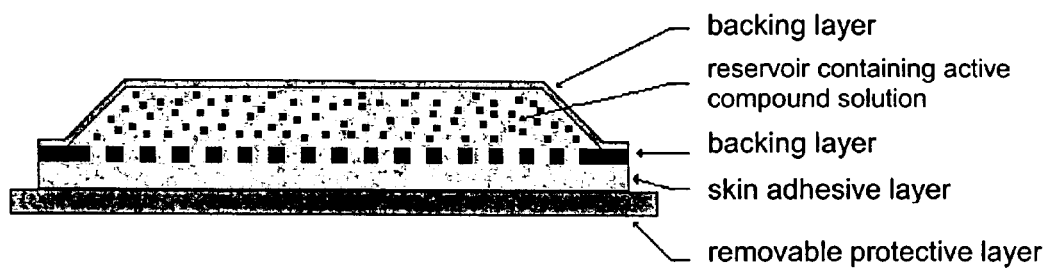
FIGS. 1-3 are diagrams showing construction of a microreservoir system.
Figure 2:
Figure 3:
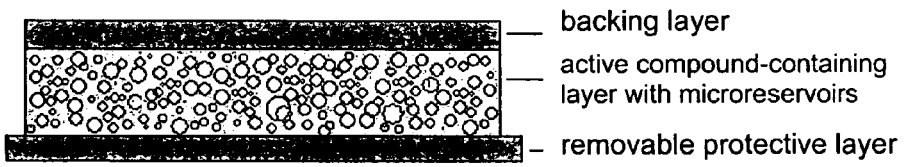

The invention relates to a drug delivery device suitable for administrating capsaicin, a capsaicin analog, or a mixture thereof. For convenience, the term "therapeutic compound" is sometimes used herein below to refer to capsaicin, capsaicin analog(s), or mixtures to be administered. In one aspect, the invention provides a drug delivery device comprising a therapeutic compound-impermeable backing layer, a self-adhesive matrix (usually a polysiloxane-based matrix) comprising individual isolated liquid microreservoir droplets ("microreservoirs") containing capsaicin or a capsaicin analog dissolved in an amphiphilic solvent, and a protective film to be removed before use of the device. The term "microreservoir system" used herein refers to the said self-adhesive matrix comprising a plurality of the said microreservoir droplets which are microdispersed in the matrix. The active compound (e.g., capsaicin) in the microreservoir droplets is dissolved at a concentration below the saturation concentration (and is thus present in completely dissolved form).

In a related aspect, the invention provides a method of treating neuropathic pain in a subject (e.g., human, non-human, primate, or mammal) in need of such treatment by applying a device of the invention.

In another related aspect, the invention provides a method of making a drug delivery device suitable for treatment of neuropathic pain.

A brief discussion of the architecture of therapeutic patches will aid in the appreciation of the present invention. Various forms of topical and transdermal patches are known for delivering an active compound (e.g., drug), the most common being "matrix systems" and "reservoir systems".

Matrix systems are characterized (in the simplest case) by a backing layer impermeable to the active compound (i.e., compound to be delivered to the subject), an active compound-containing layer and a protective layer to be removed before use. The active compound-containing layer contains the active compound completely or partially in dissolved form and is ideally self-adhesive. In more complicated embodiments, the matrix is composed of a number of layers and can include a control membrane. Suitable base polymers for a self-adhesive matrix are, for example, polyacrylates, polysiloxanes, polyurethanes or polyisobutylenes.

Reservoir systems are a type of pouch consisting of an impermeable and inert backing layer and an active compound-permeable membrane, the active compound being present in a liquid preparation in the pouch. The membrane can be a microporous film or a nonporous partition membrane. Usually, the membrane is provided with an adhesive layer that serves to adhere the system to the skin. The side facing the skin is also protected in this patch design by a film that has to be removed before use.

An advantage of the reservoir systems is that the saturation solubility of the active compound can be adjusted easily to the particular need by the choice of the solvent or solvent mixture. For thermodynamic reasons, it is advantageous for the release of active compound in and on the skin if the active compound is present in the active compound-containing parts of the patch at a concentration that is not too far below the saturation concentration. The uptake capacity of the patch for the amount of active compound needed can be adjusted in a wide range to fit the particular needs by means of adjusting the amount of active compound solution.

In matrix patches, the active compound is included in the adhesive matrix in a form that is safe from leaking, and the patch can be cut to the size using ordinary scissors. On the other hand, it is difficult under certain circumstances to adjust the solubility properties of the matrix for the active compound such that the active compound can be dissolved in the matrix in the necessary amount and also remains dissolved during the storage. In the case of a patch to deliver capsaicin or an analog, the therapeutic compound present in the matrix in undissolved form, or which recrystallizes during the storage period, makes no contribution to the release of active compound in the skin because of the desired short application period of at least most a few hours for a capsaicin patch or a patch having a capsaicin-containing active compound for the therapy of neuropathic pain.

Surprisingly, it has now been found that, for a patch for a high-dose therapy for the treatment of neuropathic pain with capsaicin or substances analogous to capsaicin, a further, lesser known patch variant, a "microreservoir system", is particularly highly suitable. No reference to such microreservoir systems can be inferred from the previously mentioned U.S. Pat. No. 6,239,180.

The invention therefore related to a topical patch comprising an active compound-impermeable backing layer, a self-adhesive matrix based on polysiloxanes containing at least 3% by weight, preferably 5% by weight, of capsaicin or active compounds analogous to capsaicin, preferably capsaicin, and a protective film to be removed before use, in which a. the matrix contains liquid microreservoirs based on an amphiphilic solvent, in which the active compound is present in completely dissolved form and
b. the concentration of the active compound in the microreservoirs is between 20 and 90% by weight, preferably 40 and 70% by weight, of the saturation concentration.

Possible amphiphilic solvents for the active compound are preferably butanediols, such as 1,3-butanediol, dipropylene glycol, tetrahydrofurfuryl alcohol, diethylene glycol dimethyl ether, diethylene glycol monoethyl ether, diethylene glycol monobutyl ether, propylene glycol, dipropylene glycol, carboxylic acid esters of tri- and diethylene glycol, polyethoxylated fatty alcohols of 6-18 C atoms or 2,2-dimethyl-4-hydroxymethyl-1,3-dioxolane (Solketal®), in particular glycol, 1,3-butanediol, dipropylene, diethylene glycol monoethyl ether or 2,2-dimethyl-4-hydroxymethyl-1,3-dioxolane or mixtures of these solvents.

The solvent or the solvent mixture of the microreservoirs can contain a viscosity-increasing additive such a cellulose derivative or a high molecular weight polyacrylic acid or its salt and/or derivatives such as esters, preferably ethylcellulose or hydroxypropylcellulose.

The proportion of the microreservoir droplets in the matrix is usually less than about 40% by weight, more often less than about 35% by weight and most often between about 20 and about 30% by weight.

Amine-resistant polysiloxanes can be used in the matrix. Preferably, a mixture of a polysiloxane of medium tack and a polysiloxane of high tack is used. The used polysiloxanes are synthesized from linear bifunctional and branched polyfunctional oligomers. The ratio of both types of oligomers determines the physical properties of the adhesives. More polyfunctional oligomers result in a more cross-linked adhesive with a higher cohesion and a reduced tack, less polyfunctional oligomers result in a higher teack and a reduced cohesion. The high tack version used in the examples is tacky enough to stick on human skin. The medium tack version is nearly not tacky at all but is useful to compensate the softening effect of other ingredients like e.g. in this case of capsaicin and the solvent of the microreservoirs. To increase the adhesive power of the matrix, this can contain 0.5-5% by weight of a silicone oil (e.g., dimethicone).

In a preferred embodiment of a topical patch according to the invention, the matrix contains at least 5% to about 10% by weight of capsaicin or capsaicin analog, 10-25% by weight of diethylene glycol monoethyl ether, 0-2% by weight of ethylcellulose, 0-5% by weight of silicone oil and 58-85% by weight of self-adhesive pressure sensitive polysiloxane. The coating weight of the matrix is usually between 30 and 200 g/m$^2$, preferably between 50 and 120 g/m$^2$. Suitable materials for the backing layer include, for example, a polyester film (e.g., 10-20 μm thick), an ethylene-vinyl acetate copolymer, and the like.

Suitable capsaicin analogs for use in the patches of the invention include naturally occurring and synthetic capsaicin derivatives and analogs ("capsaicinoids") such as, for example, those described in U.S. Pat. No. 5,762,963, which is incorporated herein by reference.

In microreservoir systems, a liquid active compound preparation is dispersed in an adhesive matrix in the form of small droplets ("microreservoirs"). The appearance of a microreservoir system is similar to a classical matrix system, and a microreservoir system can only be recognized from a typical matrix system with difficulty, since the small microreservoirs can only be recognized under the microscope. In the preceding and the following sections therefore, the active compound-containing part of the patch is also described by "matrix". The size of the resulting droplets depends on the stirring conditions and the applied shear forces during stirring. The size is very consistent and reproducable using the same mixing conditions.

It is, however, to be noted that unlike classical matrix systems, in microreservoir systems the active compound is dissolved mainly in the microreservoirs (and only to a small extent in the polymer). In this sense, microreservoir systems can be considered a mixed type of matrix patch and reservoir patch and combines the advantages of both patch variants. As in classical reservoir systems, the saturation solubility can easily be adjusted by the choice of the solvent to a valve adequate for the particular requirements, and as in classical matrix systems the patch can be divided into smaller patches using scissors without leakage.

Microreservoir systems can also include a control membrane controlling the release of active compound and excipient. However, for the specific application in the present case (i.e., having a short application time in which is as rapid release of active compound is desired) a control membrane usually not present.

Microreservoirs systems are disclosed in U.S. Pat. Nos. 3,946,106, 4,053,580, 4,814,184 and 5,145,682, each of which is incorporated herein by reference. Specific microreservoirs systems are described in international patent publication WO-A-01/01,967 the disclosure of which is incorporated herein by reference. These microreservoir systems contain, as base polymer, polysiloxanes and amphiphilic solvents for the microreservoir droplets. It has now been discovered that such microreservoir systems are particularly highly suitable, on the basis of the good solubility of capsaicin and capsaicin analogs in amphiphilic solvents such as, for example, diethylene glycol monoethyl ether, 1,3-butanediol, dipropylene glycol and Solketal, for a topical high concentration therapy using these active compounds.

A particularly highly suitable solvent has proven to be diethylene glycol monoethyl ether (DGME, also known by the trade name Transcutol®). The solubility of capsaicin in DGME is about 50% by weight, and the solubilities of capsaicin analogs structurally similar to capsaicin are comparable. This means that in order to incorporate enough active compound into the matrix, the therapeutic compound does not necessarily have to dissolve in DGME in a concentration near the saturation limit. The result is that the patch itself is not amenable to recrystallization of the therapeutic compound (e.g., capsaicin) even under unfavorable conditions, such as, for example, the partial loss of the solvent or low temperature. In practice, an about 20-35% by weight solution of capsaicin in DGME has proven particularly highly suitable. Because the saturation concentration of capsaicin in DGME is 50% by weight, this solution is 40-70% by weight of the saturation solubility. In this context, the concentration is calculated according to the following formula:

$$\text{Weight of therapeutic compound} \times 100/(\text{weight of therapeutic compound} + \text{weight of solvent})$$

An advantage of using DGME is that, in addition to the high saturation limit of capsaicin in this compound, DGME acts as a penetration enhancer. It is therefore advantageous that after application of the patch to the skin, DGME is released along with the capsaicin or analog. The simultaneous release of DGME causes the concentration, and thus also the thermodynamic activity of the therapeutic compound in the microreservoir system, to remain at a high level despite release. As the results of permeation experiments on human epidermis shown in Table 2 demonstrate, the active compound flux from such systems is approximately twice as high as that from a matrix which is supersaturated with crystalline capsaicin. This is an indication that the active compound concentration in the microreservoir system increases even above the saturation solubility and the system even becomes supersaturated with dissolved capsaicin. Because of the short application time, the therapeutic compound, however, has no opportunity to recrystallize, such that the active compound flux into the skin or the active compound dispersion into the skin is very effective. The rapid increase of the concentration of the active compound in the active compound reservoirs due to the fast release of DGME after the application of the patch is the final reason why the initial concentration of the active compound can be well below the saturation concentration without that the active compound flux is adversely affected. The absorption of moisture from the skin makes a further contribution. Because of the extremely low absorption capacity of polysiloxanes for water, moisture can only migrate into the microreservoirs. Water is a very poor solvent for capsaicin and most capsaicin analogs. As a result, the saturation concentration of the therapeutic compound in the microreservoirs is lowered and thus its thermodynamic activity of the therapeutic compound is increased.

In order that these mechanisms can be effective, it is important that diffusible substances in the polymer have a high diffusion coefficient. For this reason, polysiloxanes as base polymers are preferred to all other polymers now in use for microreservoir systems.

Polysiloxanes can be made from solvent-free two-component systems or a solution in organic solvents. For patch production, self-adhesive polysiloxanes dissolved in solvents are preferred.

These exist in two fundamentally different variants of polysiloxanes: the normal polysiloxane which have free silanol groups as shown in formula I, (I)

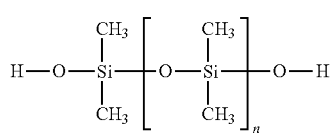

and the "amine-resistant variants", which are distinguished in that the free silanol groups are derivatized by trimethylsilyl groups. Such amine-resistant polysiloxanes have also proven suitable for therapeutic compound-containing patches without active compound and/or excipients which both do not have a basic group. Owing to the absence of free silanol groups, the solubility of active compounds in the polymer is further reduced and the diffusion coefficient is further increased for many therapeutic compounds due to the interaction with the polar free silanol groups, which is not possible. Formula I shows the structure of a linear polysiloxane molecule that is prepared from dimethylsiloxane by polycondensation. Three-dimensional crosslinking can be achieved by the additional use of methylsiloxane.

In further polysiloxanes according to the invention, the methyl groups can be completely or partially replaced by other alkyl radicals or alternatively phenyl radicals.

Without the invention being restricted thereto, the fundamental matrix composition of an embodiment of a patch according to the invention containing the therapeutic compound capsaicin can be seen from Table 1 below.

TABLE 1

Composition of the matrix of a microreservoir system for the topical high-dose therapy of capsaicin

| Component | Percent by weight |
|---|---|
| Capsaicin | 8 |
| Transcutol ® (DGME) | 20 |
| Self-adhesive polysiloxane matrix | 72 |

The thickness of the matrix is generally between about 30 and about 200 μm (corresponding to a coating weight of about 30 to about 200 g/m$^2$), but values differing therefrom can also be used depending on the properties of the specific formulation. In practice, a matrix thickness of between 50 and 100 μm has proven particularly highly suitable.

The backing layer for the patch should ideally be as impermeable or inert as possible for the therapeutic compound and DGME or the amphiphilic solvent selected. Polyester fulfills this condition, but other materials such as, for example, ethylene-vinyl acetate copolymers and polyamide are suitable. In practice, a polyester film about 20 μm thick has proven highly suitable. In order to improve the adhesion of the matrix to the backing layer, it is advantageous to siliconize the contact side of the backing layer to the matrix. Adhesives based on polyacrylates do not adhere to such siliconized films or only adhere very poorly, adhesives based on polysiloxanes, however, adhere very well on account of the chemical similarity.

As the protective film to be removed before use, a polyester film is best used which due to a specific surface treatment is repellent to adhesives based on polysiloxanes. Suitable films are supplied by a number of manufacturers and are known best to the person skilled in the art.

The self-adhesive polysiloxane matrix can be a mixture of adhesives having different adhesive behavior in order to optimize the adhesive behavior of the patch to the skin. For further improvement of the adhesive behavior, a silicone oil of suitable viscosity or molecular weight can additionally be added in a concentration of up to about 5% by weight.

The invention also relates to a process for the production of a topical patch according to the invention, which comprises dissolving the therapeutic compound in an amphiphilic solvent, adding this solution to a solution of a polysiloxane or the matrix constituents and dispersing with stirring, coating the resulting dispersion onto a protective layer which is removable and removing the solvent of the polysiloxane at elevated temperature and laminating the backing layer onto the dried layer.

The solvent for the therapeutic compound must not mix or may only mix to a small extent with the solvent for the adhesive. Suitable solvents for adhesives are, for example, petroleum ethers or alkanes such as n-hexane and n-heptane. It has been shown that the dispersion of the therapeutic compound solution can be realized more easily if the viscosity of the therapeutic compound solution is increased by the addition of a suitable agent such as, for example, a cellulose derivative such as ethylcellulose or hydroxypropylcellulose. The dispersion is now coated onto the removable protective film in a thickness, which after the removal of the solvent of the adhesive, affords a matrix layer having the desired thickness. The dried layer is now laminated with the backing layer and thus the finished patch laminate is obtained.

The patches can now be punched out of this laminate in the desired shape and size and packed into a suitable sachet of primary packing. A highly suitable primary packing has proven to be a laminate consisting of paper/glue/aluminum foil/glue/Barex®, as is described in U.S. Pat. No. RE37,934. Barex® is a heat-sealable polymer based on rubber-modified acrylonitrile copolymer, which is distinguished by a low absorptivity for volatile ingredients of patches.

The aim of the invention was the development of a patch having an optimized therapeutic compound flux into the human skin. Because the microreservoir system within the meaning of this invention has no membrane controlling the release of therapeutic compound, and also the matrix itself can exert no kinetic control on the release of therapeutic compound due to the high diffusion coefficient of the therapeutic compound in polysiloxanes, the only element controlling the release of therapeutic compound into the deeper skin layers is the skin or the uppermost layer of skin or the uppermost layer of skin, the stratum corneum. The optimization of the matrix composition was therefore consistently carried out by in vitro permeation studies using human skin and by Franz diffusion cells known to the person skilled in the art for the experimental procedure.

In a first study, the influence of DGME on the permeation rate was investigated. The results are shown in Table 2.

TABLE 2

Influence of DGME on the permeation rate of capsaicin through human epidermis[1]

| Formulation | Cumulated amount of capsaicin [μg/cm$^2$][2] after | | | | | | Permeation rate [μg/cm$^2$ * h] |
| --- | --- | --- | --- | --- | --- | --- | --- |
| | 1 h | 2 h | 3 h | 4 h | 6 h | 8 h | |
| Formulation 1[3] (with DGME) | 0.72 | 2.37 | 4.24 | 5.93 | 9.37 | 12.70 | 1.59 |
| Formulation 2[4] (without DGME) | 0.34 | 1.09 | 1.96 | 2.79 | 4.52 | 6.32 | 0.79 |

[1]Epidermis, female breast, age 37 years
[2]Mean values from 3 individual measurements each
[3]8% by weight of capsaicin and 21% by weight of DGME in amine-resistant polysiloxane matrix
[4]Matrix supersaturated with crystalline capsaicin In formulation 2, the therapeutic compound capsaicin is largely (>95% by weight) dispersed in the matrix undissolved in the form of small crystals. This means that the matrix is saturated with dissolved capsaicin and the thermodynamic activity of the therapeutic compound is maximal for a stable matrix which is not supersaturated. Formulation 1 shows a permeation rate that is approximately twice as high.

Ignoring the small amounts of capsaicin that are dissolved in the polysiloxane itself, the concentration of the capsaicin in the microreservoir droplets in formulation 1 is about 28% by weight. This is considerably below the saturation solubility of 50% by weight and guarantees that even in the case of a partial loss of the DGME or at reduced temperature there is no danger of recrystallization in the matrix. This means that before use the patch is physically stable and reaches a higher saturated or supersaturated state associated with a greatly increased permeation rate only after application.

In a second series, the influence of the capsaicin concentration on the permeation rate was investigated. The results are shown in Table 3.

TABLE 3

Influence of the capsaicin concentration on the permeation rate through human epidermis[1]

| Formulation[3] | Cumulated amount of capsaicin [μg/cm$^2$][2] after | | | | | | Permeation rate [μg/cm$^2$ * h] |
| --- | --- | --- | --- | --- | --- | --- | --- |
| | 1 h | 2 h | 3 h | 4 h | 6 h | 8 h | |
| Formulation 3 4% by weight of capsaicin | 0.32 | 0.69 | 1.0 | 1.44 | 2.15 | 2.98 | 0.37 |
| Formulation 4 6% by weight of capsaicin | 0.30 | 0.74 | 1.40 | 1.71 | 2.77 | 3.93 | 0.49 |
| Formulation 5 8% by weight of capsaicin | 0.54 | 1.02 | 1.72 | 2.37 | 3.44 | 4.64 | 0.58 |

[1]Epidermis, female breast, age 47 years
[2]Mean values from 3 individual measurements
[3]DGME concentration 21% by weight The permeation rate shows a marked dependence on the capsaicin concentration, i.e. the release rate of the patch can be adjusted easily to the value necessary for capsaicin or capsaicin analog via the concentration in DGME (or the solvent intended for the microreservoirs).

A capsaicin concentration of about 8% by weight (e.g., about 5% to about 10% by weight, usually 7% to 9% by weight) in combination with a DGME concentration of about 15% to about 25% by weight has proven particularly highly suitable.

A therapeutic compound-containing matrix optimized with respect to the adhesive behavior on the skin and the other physical properties has the following composition:

TABLE 4

Optimized composition of the matrix of a microreservoir system for topical high-dose therapy using capsaicin

| Component | Percent by weight |
| --- | --- |
| capsaicin | 8 |
| DGME | 20 |
| Ethylcellulose | 0.8 |
| High-tack amine-resistant polysiloxane BIO-PSA 4301, Dow Corning | 21 |
| Medium-tack amine-resistant polysiloxane BIO-PSA 4201, Dow Corning | 49 |
| Silicone oil, 12,500 cSt | 2 |
| Coating weight | 80 g/m$^2$ |

Patches within the meaning of this invention containing the therapeutic compound capsaicin have proven very effective in appropriate clinical studies. Even a one-hour treatment of the affected areas reduced the sensation of pain significantly, the action lasting for weeks. The patches in this case proved to be highly tolerable and were very well accepted by the patients. In summary, it can thus be said that patches within the meaning of this invention are optimally suitable for treatment of neuropathic pain described in U.S. Pat. No. 6,248,788 using high concentration of capsaicin or capsaicin analogs.

The invention therefore also relates to use of a topical patch according to the invention for the treatment of neuropathic pain and other conditions.

Use of the Capsaicin or Capsaicin Analog Patch

This section describes use of the invention. However, it will be understood that the examples in this section are provided for illustration and not limitation. Capsaicin application has numerous therapeutic benefits, each of which can be effectively treated using the methods of the invention. Conditions for which capsaicin or capsaicin analog treatment may be indicated include neuropathic pain (including pain associated with diabetic neuropathy, postherpetic neuralgia, HIV/AIDS, traumatic injury, complex regional pain syndrome, trigeminal neuralgia, erythromelalgia and phantom pain), pain produced by mixed nociceptive and/or neuropathic mixed etiologies (e.g., cancer, osteoarthritis, fibromyalgia and low back pain), inflammatory hyperalgesia, interstitial cystitis, dermatitis, pruritis, itch, psoriasis, warts, and headaches. Generally, the capsaicin- or capsaicin analog-containing patches can be used to treat any condition for which topical administration of capsaicin is beneficial.

EXAMPLES

The following examples serve to illustrate the invention without the latter having to be restricted thereto.

Example 1

Production of a Patch Containing Capsaicin 250 g of DGME are initially thickened with 4.5 g of ethylcellulose with stirring. 97 g of capsaicin is then added and completely dissolved with stirring. 286 g of the above therapeutic compound solution is added to 1000 g of a solution of the polysiloxane or the mixture of the polysiloxanes in n-heptane having a solids content of 70% by weight and dispersed in the adhesive solution with intensive stirring.

Subsequently, using a suitable coating process, the dispersion is coated onto a removable protective film and is suitable for polysiloxane adhesives, e.g. Scotchpak® 1022 from 3M, in a thickness such that the coating weight after the removal of the n-heptane is 80 g/m². The dried film is then laminated with the backing layer, e.g. polyester film 20 μm thick, and the finished patch is punched out of the complete laminate. The punched patches are then sealed into a sachet of a suitable primary packing laminate.

The temperatures under which the solvent of the adhesive, n-heptane, is removed, should ideally not exceed 40° C. There is more DGME in the final bulk mixture than in the final composition due to loss of DGME during the drying process.

Example 2

196 g of DGME is initially thickened with 4 g of ethylcellulose with stirring. 30 g of nonivamide (pelargonic acid vanillylamide) are then added and completely dissolved with stirring.

The solution is then added to 1000 g of a solution of the polysiloxane or the mixture of the polysiloxanes in n-heptane having a solids content of 70% by weight and dispersed in the adhesive solution with intensive stirring.

Subsequently, using a suitable coating process, the dispersion is coated onto a removable protective film, e.g. Scotchpak® 1022 from 3M, in a thickness such that the coating weight after the removal of the n-heptane is 100 g/m². The dried film is then laminated with the backing layer, e.g. polyester film 20 μm thick, and the finished patch is punched out of the complete laminate. The punched patches are then sealed into a sachet of a suitable primary packaging.

Example 3

200 g of dipropyleneglycol are thickened with 2 g of hydroxyethylcellulose with stirring. 60 g of capsaicin is then added and completely dissolved with stirring. The solution is then added to 1000 g of a solution of the polysiloxane or the mixture of the polysiloxanes in n-heptane having a solids content of 70% by weight and dispersed in the adhesive solution with intensive stirring.

Subsequently, using a suitable coating process, the dispersion is coated onto a removable protective film, e.g. Scotchpak® 1022 from 3M, in a thickness such that the coating weight after the removal of the n-heptane is 100 g/m². The dried film is then laminated with the backing layer, e.g. polyester film 20 μm thick, and the finished patch is punched out of the complete laminate. The punched patches are then sealed into a sachet of a suitable primary packaging.

Example 4

Same procedure as described in example 1 but olvanil (oleyl vanillylamide) is used instead of capsaicin.

Example 5

36 g of nonivamide is dissolved in 164 g of Solketal with stirring. The solution is then added to 1000 g of a solution of the polysiloxane or the mixture of the polysiloxanes in n-heptane having a solids content of 70% by weight and dispersed in the adhesive solution with intensive stirring.

Subsequently, using a suitable coating process, the dispersion is coated onto a removable protective film, e.g. Scotchpak® 1022 from 3M, in a thickness such that the coating weight after the removal of the n-heptane is 100 g/m². The dried film is then laminated with the backing layer, e.g. polyester film 20 μm thick, and the finished patch is punched out of the complete laminate. The punched patches are then sealed into a sachet of a suitable primary packaging.

The invention claimed is:
1. A topical patch comprising
a therapeutic compound-impermeable backing layer,
a self-adhesive amine-resistant polysiloxane matrix consisting of:
(i) a therapeutic compound for treating neuropathic pain consisting of about 5%-about 10% by weight of capsaicin or a capsaicin analog or mixture thereof as the therapeutic compound, based on the total weight of the matrix; and
(ii) about 10%-about 25% by weight of diethylene glycol monoethyl ether (DGME) based on the total weight of the matrix,
wherein the polysiloxane matrix is a mixture of a polysiloxane of medium tack and a polysiloxane of high tack,
wherein the matrix contains from about 0.5 to about 5% by weight of a silicone oil,
wherein the matrix comprises 58-85% by weight of self adhesive polysiloxane and the coating weight of the matrix is between 30 and 200 g/m², and
a protective film to be removed before use,
in which
a. the matrix contains liquid microreservoir droplets comprising an amphiphilic solvent, in which the therapeutic compound is dissolved, wherein the microreservoir droplets are in an amount between 20 and 40% by weight, based on the total weight of the matrix,
wherein the microreservoir droplets comprise a viscosity-increasing additive dissolved in the solvent, and b. the concentration of the therapeutic compound in the microreservoir droplets is between 40 and 70% by weight of the saturation concentration, wherein the amphiphilic solvent is diethylene glycol monoethyl ether.

2. The topical patch as claimed in claim 1, in which the viscosity-increasing additive is a cellulose derivative or a high molecular weight polyacrylic acid.

3. The topical patch of claim 2, in which the viscosity-increasing additive is ethylcellulose or hydropropylcellulose.

4. The topical patch as claimed in claim 1, in which the self-adhesive amine-resistant polysiloxane matrix contains a proportion of the microreservoir droplets in the matrix of between 20 and 30% by weight, based on the total weight of the matrix.

5. The topical patch as claimed in claim 1, in which the matrix consists of
- 5-10% by weight of capsaicin or a capsaicin analog,
- 10-25% by weight of diethylene glycol monoethyl ether,
- 0-2% by weight of ethylcellulose,
- 0-5% by weight of silicone oil, and
- 58-85% by weight of self-adhesive polysiloxane and the coating weight of the matrix is between 30 and 200 g/m$^2$.

6. The topical patch as claimed in claim 5, in which the matrix consists of
- 5-10% by weight of capsaicin,
- 10-25% by weight of diethylene glycol monoethyl ether,
- 0-2% by weight of ethylcellulose,
- 0-5% by weight of silicone oil, and
- 58-85% by weight of self-adhesive polysiloxane and the coating weight of the matrix is between 50 and 120 g/m$^2$.

7. The topical patch as claimed in claim 1, in which the backing layer consists of a polyester film 10-20 μm thick.

8. The topical patch as claimed in claim 1, in which the backing layer consists of an ethylene-vinyl acetate copolymer.

9. A method for the treatment of neuropathic pain which comprises administering the topical patch of claim 1 to a patient in need thereof.

10. The topical patch as claimed in claim 4, in which the viscosity-increasing additive is ethylcellulose or hydropropylcellulose.

11. A method for the production of a topical patch as claimed in claim 1, which comprises dissolving the therapeutic compound in an amphiphilic solvent, adding this solution to a solution of a polysiloxane or the matrix constituents and dispersing, coating the resulting dispersion onto a protective layer which is removable again and removing the solvent of the polysiloxane and laminating the backing layer onto the dried matrix layer.

12. The topical patch as claimed in claim 1, in which the matrix comprises 8% by weight capsaicin.

13. The topical patch as claimed in claim 12, in which the matrix contains ethylcellulose and silicone oil, wherein the silicone oil is dimethicone.

14. The method of claim 9 wherein administration of the topical patch of claim 1 to a patient in need thereof is over a period of 1 to 3 hours.

15. The method of claim 14 wherein administration of the topical patch of claim 1 to a patient in need thereof is over a period of 1 hour.

* * * * *